(12) United States Patent
Dave et al.

(10) Patent No.: US 6,417,373 B1
(45) Date of Patent: Jul. 9, 2002

(54) PREPARATIONS OF AZABICYLOBUTANE, PRECURSORS, AND RELATED COMPOSITIONS

(75) Inventors: Paritosh R. Dave, Bridgewater, NJ (US); Thomas G. Archibald, Fair Oaks, CA (US)

(73) Assignee: The United States of America as represented by Secretary of Army, Washington, DC (US)

( * ) Notice: Subject to any disclaimer, the term of this patent is extended or adjusted under 35 U.S.C. 154(b) by 0 days.

(21) Appl. No.: 09/175,149

(22) Filed: Oct. 19, 1998

Related U.S. Application Data

(62) Division of application No. 08/441,512, filed on May 15, 1995, now Pat. No. 5,824,807.

(51) Int. Cl.$^7$ .............................................. C07D 205/04
(52) U.S. Cl. ...................................................... 548/952
(58) Field of Search ......................................... 548/952

(56) References Cited

FOREIGN PATENT DOCUMENTS

DE          1802209    *   5/1970

* cited by examiner

*Primary Examiner*—Laura L. Stockton
(74) *Attorney, Agent, or Firm*—John F. Moran; Michael Sachs; John E. Callaghan

(57) ABSTRACT

New aza azetidinium sulfate compounds are described which can be intermediates in the preparation of azabicyclobutane.

1 Claim, 1 Drawing Sheet

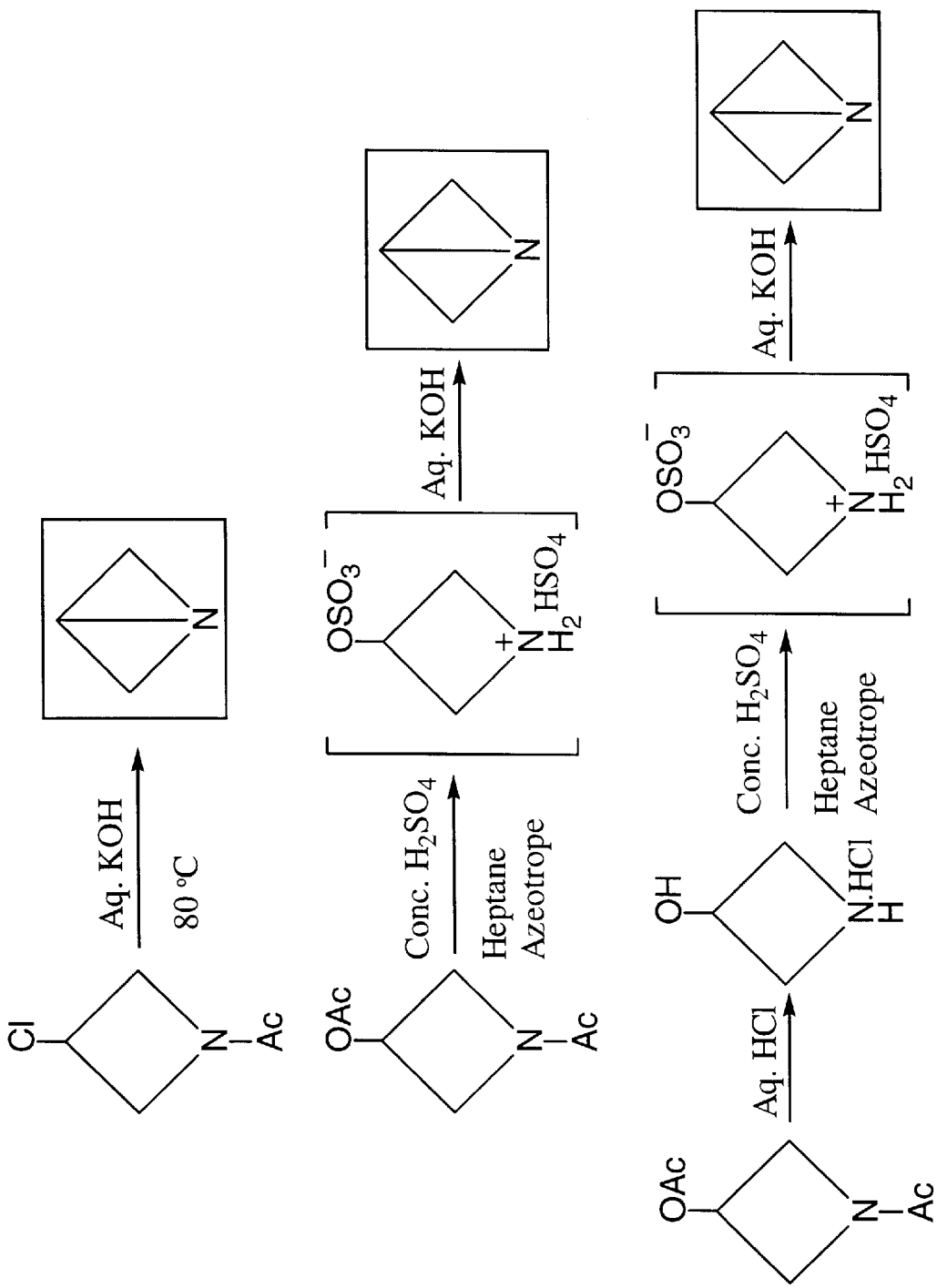
Figure

PREPARATIONS OF AZABICYLOBUTANE, PRECURSORS, AND RELATED COMPOSITIONS

This application is a division of Ser. No.08/441,512, filed May 15, 1995, now U.S. Pat. No. 5,824,807.

STATEMENT OF GOVERNMENT INTEREST

The invention described herein may be manufactured, used or licensed by or for the United States Government for governmental purposes without payment to the inventors of any royalties.

STATEMENT OF RELATED APPLICATIONS

This application is a division of the U.S. Patent Applications described below. The subject matter of this application is disclosed in the several applications and in the copending applications that were included by reference therein. The applications are:
DAR 4-94A Ser. No. 08/440,947 now U.S. Pat. No. 5,808,099
DAR 4-94A1 pending
DAR 4-94B Ser. No. 08/440,946 now U.S. Pat. No. 5,824,806
DAR 4-94B1 pending
DAR 4-94C Ser. No. 08/440,945 now abandoned
DAR 4-94C1 pending
DAR 4-94D Ser. No. 08/441,511 U.S. Pat. No. 5,580,988
DAR 4-94D1 pending
DAR 4-94E Ser. No. 08/441,512 now U.S. Pat. No. 5,824,807

BACKGROUND OF INVENTION

Azetidines are four member ring compounds having one nitrogen and three carbon atoms. As a four member ring, there is ring strain which leads to difficulties in preparation of the azetidines and more difficulties in substitutions and modifications of azetidines. The compounds are of importance as intermediates leading to 1,3,3 trinitroazetidine, TNAZ, an energetic material that can be melt cast or press loaded into articles for use as an explosive or propellant. One route to TNAZ uses azabicylobutane as an intermediate. This compound has bridgehead nitrogen and three carbon atoms in its ring. Azabicyclobutane is difficult to prepare and tends to decompose. The solid compound can be dangerous to handle.

SUMMARY OF INVENTION

This application concerns new processes for the preparation of azabicylobutane, new compounds that can be used as intermediates in the preparation of azabicylobutane and compositions to prepare azabicylobutane in situ.

BRIEF DESCRIPTION OF DRAWINGS

The Figure shows the preparation of the azabicylobutane and the new compounds and compositions of this invention which include certain substituted azetidines and the use of these azetidines to make TNAZ.

DETAILED DESCRIPTION OF THE INVENTION AND DRAWING

In general, the process of the invention proceeds by reacting an aza substituted,3-substituted azetidine under conditions to cause elimination of the substituents at the aza and 3- positions. The aza substituent can be an acyl group or a sulfate ester. The reaction conditions are very clean in the sense that the product is an aqueous solution of the azabicylobutane in innocuous salts. The solution can be used "as is" as the source of azabicylobutane or the azabicyclobutane can be recovered from it. The yields of the process are very high.

Another alternative is to prepare solutions of the precursors and to conduct the elimination reactions at the point when the azabicylobutane is needed. This is an in-situ preparation which can reduce the dangers of decomposition of the azabicylobutane.

The Figure illustrates the several processes to prepare azabicylobutane. In the first reaction scheme, N-acyl,3-haloazetidine is reacted with aqueous alkali at moderate temperatures to cause elimination of the acyl group and the halide atom to effect the cyclization between the aza nitrogen and the 3- position carbon atom. The specific reactant, N-acetyl,3-chloroazetidine gives a very clean reaction product in the form of azabicyclobutane in water with non-deleterious salts.

Another alternate process shown in the Figure starts with an N-acyl,3-acyloxy azetidine. It is reacted with sulfuric acid to form an intermediate compound. The intermediate is an azetidine with a protonated aza hydrogen sulfate and a 3-sulfate ester. On treatment with aqueous alkali, the elimination occurs at the aza and 3- positions to give the azabicylobutane product.

A third process starts with the N-acetyl,3-acetyloxyazetidine. It is hydrolyzed with hydrochloric acid to the quaternary aza hydrochloride salt of the azetidine with hydroxyl at the 3- position. This is converted to the sulfate ester as described above. The sulfate ester is reacted with aqueous alkali to form the azabicyclobutane.

These processes are under mild conditions and give high yields of product. As discussed, the reaction product is in an aqueous media and can be used as such or can be recovered from the reaction medium. The processes are easy enough to conduct that the reaction can be performed on site to provide in situ production of the azabicyclobutane as a reaction step in processes which use the azabicyclobutane. It can be seen that the acetyl group has the advantage that it readily leaves the azetidinyl skeleton in the cyclization mechanism. Sulfate acts in a similar manner.

As new compositions, this invention has the sulfate esters of the azetidines as new compounds. The copending related applications also cover new azetidine compounds and the processes of preparation. The N-acetyl,3-chloroazetidine is an example of such a compound.

It can be seen that the compounds and processes are capable of wide variation and modification. The new compounds and the efficiencies achieved with the invention are important contributions. However, while the preferred embodiments have been described with reference to particular features, sequences of steps, functional groups and other ring substituents and proportions, it is intended that this invention shall cover such structures, applications and uses as those in the field would deem equivalents.

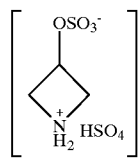

We claim:
1. The compound